(12) United States Patent
Plata et al.

(10) Patent No.: US 9,468,592 B2
(45) Date of Patent: Oct. 18, 2016

(54) TOOTHPASTE COMPOSITION

(71) Applicant: Colgate-Palmolive Company, New York, NY (US)

(72) Inventors: Rolando Plata, Guangzhou (CN); Xiaojing Lu, Guangzhou (CN); Yuyan Zeng, Guangzhou (CN); Chengkang Tan, Guangzhou (CN)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 14/429,907

(22) PCT Filed: Oct. 19, 2012

(86) PCT No.: PCT/CN2012/083249
§ 371 (c)(1),
(2) Date: Mar. 20, 2015

(87) PCT Pub. No.: WO2014/059678
PCT Pub. Date: Apr. 24, 2014

(65) Prior Publication Data
US 2015/0238395 A1    Aug. 27, 2015

(51) Int. Cl.
*A61K 8/19* (2006.01)
*A61K 8/73* (2006.01)
*A61Q 11/00* (2006.01)

(52) U.S. Cl.
CPC ............... *A61K 8/19* (2013.01); *A61K 8/731* (2013.01); *A61K 8/737* (2013.01); *A61Q 11/00* (2013.01); *A61K 2800/30* (2013.01); *A61K 2800/88* (2013.01)

(58) Field of Classification Search
CPC ...................................................... A61Q 11/00
USPC ...................................................... 424/49, 54
See application file for complete search history.

(56) References Cited

U.S. PATENT DOCUMENTS

| 4,828,833 A * | 5/1989 | Cordon ............................ 424/54 |
| 5,030,444 A | 7/1991 | Hoyles et al. |
| 6,045,780 A | 4/2000 | Bixler et al. |
| 6,126,923 A | 10/2000 | Burke et al. |
| 2004/0001815 A1 | 1/2004 | Cheung |
| 2004/0018155 A1 * | 1/2004 | Hoagland ........................ 424/49 |
| 2005/0244346 A1 | 11/2005 | Nakao et al. |
| 2012/0261300 A1 | 10/2012 | Schapiro et al. |

FOREIGN PATENT DOCUMENTS

| CN | 102058505 A | 5/2011 |
| CN | 102274144 A | 12/2011 |
| CN | 102670442 A | 9/2012 |
| EP | 0368130 | 5/1990 |

OTHER PUBLICATIONS

International Search Report and Written Opinion in International Application No. PCT/CN2012/083249, mailed Aug. 1, 2013.
Romano et al., "Industrial applications of polysaccharides" Rheology of Industrial Polysaccharides: Theory and applications, Jan. 1995, pp. 134-161.

* cited by examiner

*Primary Examiner* — Walter Webb

(57) ABSTRACT

Described herein are toothpaste compositions comprising an orally acceptable vehicle; calcium carbonate; and a binder system comprising guar gum and at least one cellulose polymer.

17 Claims, No Drawings

US 9,468,592 B2

TOOTHPASTE COMPOSITION

BACKGROUND

Various binder components, and binder systems incorporating combinations of binder components, are known in the toothpaste art. Different binder components impart different rheological properties to the toothpaste. Cellulose polymers, in particular carboxymethyl cellulose (CMC), are widely used in toothpastes to act as a binder and thickener. However, for some toothpaste formulations, in particular toothpaste formulations containing a significant proportion of calcium carbonate particles, the addition of such a cellulose polymer can cause the toothpaste to exhibit a "stringy" effect and to exhibit "tailing" when the toothpaste is being manufactured. Such a stringy effect and tailing are manifested, for example, when the paste is mixed using a mixing blade and, after the blade has been lifted from the a mixer tank, paste on the blade falls downwardly under gravity as "tails" rather than being bound to the blade as a single non-flowing paste body.

There is a problem to fill the toothpaste package effectively and reliably if the toothpaste exhibits the stringy effect and tailing, particularly for toothpaste formulations containing a significant proportion of calcium carbonate particles.

There is accordingly a need in the art for a toothpaste composition which contains calcium carbonate particles and exhibits good rheological properties, in particular reduced stringiness and reduced tailing.

In addition, the binder component in the toothpaste has a significant impact on the stripe quality of the extruded strip to form a stable extrudable paste including the abrasive particles and the liquid phase. In striped toothpaste formulations containing a significant proportion of calcium carbonate particles, it is known to use a binder system which controls the stripe quality. In particular, is it is known to use a binder system incorporating the combination of carboxymethyl cellulose (CMC) and magnesium aluminium silicate (MAS) to provide a high stripe quality. However, the use of magnesium aluminium silicate (MAS) suffers from the problem that currently there are only a few qualified suppliers of toothpaste-grade magnesium aluminium silicate (MAS), which increases the cost and complexity of the supply chain.

There is accordingly a need in the art for a striped toothpaste composition which exhibits high stripe quality but avoids the supply chain problems of the known binder system incorporating the combination of carboxymethyl cellulose (CMC) and magnesium aluminium silicate (MAS).

SUMMARY

In some embodiments, the present invention provides a toothpaste composition which contains calcium carbonate particles and exhibits good rheological properties, in particular reduced stringiness and reduced tailing.

Some embodiments provide a two-phase toothpaste composition which contains calcium carbonate particles and exhibits high stripe quality, and is substantially free of magnesium aluminium silicate (MAS).

According to one aspect of this invention, there is provided a toothpaste composition comprising an orally acceptable vehicle, an abrasive comprising calcium carbonate particles and a binder system comprising guar gum and at least one cellulose polymer.

Optionally, the guar gum is present in an amount of from 0.05 to 0.4 wt % based on the weight of the composition, further optionally from 0.1 to 0.2 wt % based on the weight of the composition. Typically, the guar gum is present in an amount of from 0.13 to 0.17 wt % based on the weight of the composition. Most typically, the guar gum is present in an amount of about 0.15 wt % based on the weight of the composition.

In some embodiments, the guar gum is raw guar gum or is chemically unmodified guar gum.

Optionally, the calcium carbonate particles are present in an amount of from 20 to 60 wt % based on the weight of the composition, further optionally from 35 to 50 wt % based on the weight of the composition. Typically, the calcium carbonate particles are present in an amount of from 40 to 45 wt % based on the weight of the composition. Most typically, the calcium carbonate particles are present in an amount of about 42 wt % based on the weight of the composition.

Optionally, the at least one cellulose polymer is selected from one or more of hydroxypropylmethyl cellulose (HPMC), hydroxyethylpropyl cellulose (HEPC), hydroxybutylmethyl cellulose (HBMC), and carboxymethyl cellulose (CMC). Typically, the at least one cellulose polymer comprises carboxymethyl cellulose (CMC). The at least one cellulose polymer may be present as a salt, for example the sodium salt, such as sodium carboxymethyl cellulose.

Optionally, the at least one cellulose polymer is present in an amount of from 0.5 to 2.5 wt % based on the weight of the composition, further optionally, from 0.75 to 1.5 wt % based on the weight of the composition.

In one preferred embodiment, the guar gum is present in an amount of about 0.15 wt % based on the weight of the composition and carboxymethyl cellulose (CMC) is present in an amount of about 1 wt % based on the weight of the composition.

Optionally, the binder system does not comprise any magnesium aluminum silicate.

Optionally, the orally acceptable vehicle comprises sorbitol which is present in an amount of from 10 to 25 wt % based on the weight of the composition, further optionally from 12 to 18 wt % based on the weight of the composition.

Optionally, the toothpaste composition further comprises sodium monofluorophosphate in an amount of from 0.75 to 1.5 wt % based on the weight of the composition. Optionally, the toothpaste composition further comprises a thickener comprising silica particles in an amount of from 1 to 3 wt % based on the weight of the composition. Optionally, the toothpaste composition further comprises titanium dioxide in an amount of from 0.05 to 0.15 wt % based on the weight of the composition.

According to another aspect of this invention, there is provided a two-phase toothpaste packaged in a package for forming a striped strip when the toothpaste is extruded as a strip from the package, at least one of the two phases of the two-phase toothpaste comprising the toothpaste composition according to the invention.

Optionally, the two-phase toothpaste comprises a first white phase of the two-phase toothpaste, the first white phase having the toothpaste composition according to the invention and a second colored phase.

Optionally, the second colored phase comprises a toothpaste composition according to the invention and a colorant.

According to another aspect of this invention, there is provided the use, in a striped toothpaste including a white toothpaste phase comprising calcium carbonate particles as an abrasive and a colored phase, of a binder system in the white toothpaste phase which comprises guar gum and at least one cellulose polymer for minimizing mixing of the white toothpaste phase and the colored phase after the striped toothpaste has been extruded as a strip from a package.

Optionally, the guar gum is present in an amount of from 0.13 to 0.17 wt % based on the weight of the white toothpaste phase, the at least one cellulose polymer is present in an amount of from 0.75 to 1.5 wt % based on the weight of the white toothpaste phase, and the calcium carbonate particles are present in an amount of from 40 to 45 wt % based on the weight of the white toothpaste phase.

Optionally, the guar gum is raw guar gum or chemically unmodified guar gum. Optionally, the at least one cellulose polymer comprises carboxymethyl cellulose (CMC).

The compositions may contain additional therapeutic and non-therapeutic components.

This invention is predicated on the finding by the present inventors that in toothpaste comprising calcium carbonate particles as an abrasive, a binder system which comprises guar gum and at least one cellulose polymer can reduce the stringy and tailing problems of known toothpastes and, when used in particular in striped toothpaste comprising calcium carbonate particles as an abrasive, can provide a high stripe quality.

DETAILED DESCRIPTION

It should be understood that the detailed description and specific examples, while indicating embodiments of the invention, are intended for purposes of illustration only and are not intended to limit the scope of the invention.

As referred to herein, all compositional percentages are by weight of the total composition, unless otherwise specified.

As used herein, the phrase "substantially free" means that the particular component comprises less than 10% of a particular component. For example, a binder system is "substantially free" of magnesium aluminium silicate refers to a binder system that comprises less than 10% of magnesium aluminium silicate.

As used herein, the terms "calcium carbonate" and "calcium carbonate particles" are used interchangeably.

In some embodiments, the present invention provides a toothpaste composition comprising an orally acceptable vehicle, an abrasive comprising calcium carbonate particles and a binder system comprising guar gum and at least one cellulose polymer.

In the binder system, optionally the guar gum is present in an amount of from 0.05 to 0.4 wt % based on the weight of the composition, further optionally from 0.1 to 0.2 wt % based on the weight of the composition. Typically, the guar gum is present in an amount of from 0.13 to 0.17 wt % based on the weight of the composition. Most typically, the guar gum is present in an amount of about 0.15 wt % based on the weight of the composition.

In some embodiments, the guar gum is raw guar gum or is chemically unmodified guar gum.

In some embodiments, the at least one cellulose polymer is present as a salt. In some embodiments, the salt is a sodium salt.

Some embodiments of the present invention provide compositions wherein the binder system is substantially free of the magnesium aluminium silicate. In some embodiments, the binder system comprises less than 7.5% magnesium aluminium silicate. In some embodiments, the binder system comprises less than 5% magnesium aluminium silicate. In some embodiments, the binder system comprises less than 4% magnesium aluminium silicate. In some embodiments, the binder system comprises less than 3% magnesium aluminium silicate. In some embodiments, the binder system comprises less than 2% magnesium aluminium silicate. In some embodiments, the binder system comprises less than 1% magnesium aluminium silicate. In some embodiments, the binder system comprises less than 0.5% magnesium aluminium silicate.

In the binder system, optionally the at least one cellulose polymer is selected from one or more of hydroxypropylmethyl cellulose (HPMC), hydroxyethylpropyl cellulose (HEPC), hydroxybutylmethyl cellulose (HBMC), and carboxymethyl cellulose (CMC). Typically, the at least one cellulose polymer comprises carboxymethyl cellulose (CMC), for example in the form of sodium carboxymethyl cellulose. In one embodiment the at least one cellulose polymer comprises a mixture of cellulose materials having different molecular weight.

Optionally, the at least one cellulose polymer is present in an amount of from 0.5 to 2.5 wt % based on the weight of the composition, further optionally, from 0.75 to 1.5 wt % based on the weight of the composition.

In one preferred embodiment, the guar gum is present in an amount of about 0.15 wt % based on the weight of the composition and carboxymethyl cellulose (CMC) is present in an amount of about 1 wt % based on the weight of the composition.

Optionally, the binder system does not comprise any magnesium aluminum silicate.

In addition to the cellulose and guar gum binders, the toothpaste compositions of the invention may also include a polymeric adherent material that attaches to the surface of a mammalian tooth and/or to the heterogeneous biofilm which also may be present on a tooth's surface. Attachment may occur by any means, such as ionic interaction, van der Waals forces, hydrophobic-hydrophilic interactions, etc. The adherent material may be, for example, any homopolymers or copolymers (hereinafter referred to collectively as a "polymers") that adhere to the surface of a tooth.

For example, the toothpaste composition may additionally include poly(ethylene oxide) polymers (such as POLYOX from Dow Chemical), linear PVP and cross-linked PVP, PEG/PPG copolymers (such as BASF Pluracare L1220), ethylene oxide (EO)-propylene oxide (PO) block copolymers (such as polymers sold under the trade mark Pluronic available from BASF Corporation), ester gum, shellac, pressure sensitive silicone adhesives (such as BioPSA from Dow-Corning), methacrylates, or mixtures thereof. In an embodiment, a copolymer comprises (PVM/MA). In an embodiment, a copolymer comprises poly(methylvinylether/maleic anhydride). In another embodiment, a copolymer comprises poly(methylvinylether/maleic acid). In another embodiment, a copolymer comprises poly(methylvinylether/maleic acid) half esters. In another embodiment, a copolymer comprises poly(methylvinylether/maleic acid) mixed salts.

Polymers of any molecular weight may be used, including, for example molecular weights of 50,000 to 500,000, 500,000 to 2,500,000 or 2,500,000 to 10,000,000 (calculated by either number average or weight average).

Commercially-available polymers may be used in the present invention. It is understood that over time, the exact size, weight and/or composition of a commercially-available polymer may change. Based on the disclosure set forth herein, the skilled artisan will understand how to determine whether such polymers are useful in the invention.

In addition to the guar gum and at least one cellulose polymer, the toothpaste composition may additionally include, other gum bases or thickening agents, such as carrageenan (Iris moss), xanthan gum, starch, polyvinyl pyrrolidone and amorphous silicas, or any combination thereof.

In the abrasive system, optionally the calcium carbonate particles are present in an amount of from 20 to 60 wt % based on the weight of the composition, further optionally from 35 to 50 wt % based on the weight of the composition. Typically, the calcium carbonate particles are present in an amount of from 40 to 45 wt % based on the weight of the composition. Most typically, the calcium carbonate particles are present in an amount of about 42 wt % based on the weight of the composition. The calcium carbonate may comprise precipitated calcium carbonate.

The toothpaste compositions may further comprise, in addition to the calcium carbonate particles, one or more abrasive particulates. Any abrasive particulates may be used and may be selected from sodium bicarbonate, calcium phosphate (e.g., dicalcium phosphate dihydrate), calcium pyrophosphate calcium sulfate, silica, iron oxide, aluminium oxide, perlite, plastic particles, e.g., polyethylene, and combinations thereof. Any type of silica may be used, such as hydrated silica, precipitated silica or silica gel. Optionally, the toothpaste composition further comprises, as a thickener and also as an abrasive, silica particles in an amount of from 1 to 3 wt % based on the weight of the composition.

In an embodiment, the toothpaste composition comprises silica that has a particle size and an amount and distribution in the toothpaste composition so that the silica has a dual function, and functions not only as a dentin tubule-occluding particulate but also as an abrasive particulate. Such a dual function particulate may be provided by a commercially available silica such as INEOS AC43, available in commerce from Ineos Silicas, Warrington, United Kingdom. In an embodiment, such silica has a median particle size less than 8 μm, for example from 3 μm to 5 μm.

The compositions of the present invention may further comprise an abrasive useful for example as a polishing agent. Any orally acceptable abrasive can be used, but type, fineness, (particle size) and amount of abrasive should be selected so that tooth enamel is not excessively abraded in normal use of the composition. Suitable abrasives include silica, for example in the form of precipitated silica or as admixed with alumina, insoluble phosphates, and mixtures thereof. Among insoluble phosphates useful as abrasives are orthophosphates, polymetaphosphates and pyrophosphates. Illustrative examples are dicalcium orthophosphate dihydrate, calcium pyrophosphate, calcium pyrophosphate, tricalcium phosphate, calcium polymetaphosphate and insoluble sodium polymetaphosphate.

In an embodiment, the abrasive particles may be initially present in the toothpaste composition having the desired particle size, or may be initially present in the composition at a larger size, so long as the structure of the particles is such that it fractures or breaks into the desired particle size upon application of mechanical force by, e.g., a toothbrush, when brushing.

The dentifrice composition according to the invention comprises an orally acceptable vehicle. As used herein, an "orally acceptable vehicle" refers to a material or combination of materials that are safe for use in the compositions of the invention, commensurate with a reasonable benefit/risk ratio.

The composition may contain any conventional excipients or carriers, although these will vary depending on the dosage form or means of dosage selected. Excipients or carriers can include, for example, humectants, glycerin, sorbitol, xylitol, and/or propylene glycol, water or other solvents.

Surfactants may be included, if desired. Examples of suitable surfactants include water-soluble salts of higher fatty acid monoglyceride monosulfates, such as the sodium salt of monosulfated monoglyceride of hydrogenated coconut oil fatty acids; higher alkyl sulfates such as sodium lauryl sulfate; alkyl aryl sulfonates such as sodium dodecyl benzene sulfonate; higher alkyl sulfoacetates, such as sodium lauryl sulfoacetate; higher fatty acid esters of 1,2-dihydroxypropane sulfonate; and the substantially saturated higher aliphatic acyl amides of lower aliphatic amino carboxylic compounds, such as those having 12-16 carbons in the fatty acid, alkyl or acyl radicals; and the like. Examples of the last mentioned amides include N-lauryl sarcosine, and the sodium, potassium and ethanolamine salts of N-lauryl, N-myristoyl, or N-palmitoyl sarcosine. Others include, for example, nonanionic polyoxyethylene surfactants, such as Polyoxamer 407, Steareth 30, Polysorbate 20, and castor oil; and amphoteric surfactants, such as cocamidopropyl betaine (tegobaine), and cocamidopropyl betaine lauryl glucoside; condensation products of ethylene oxide with various hydrogen containing compounds that are reactive therewith and have long hydrocarbon chains (e.g., aliphatic chains of from 12 to 20 carbon atoms), which condensation products (ethoxamers) contain hydrophilic polyoxyethylene moieties, such as condensation products of poly(ethylene oxide) with fatty acids, fatty, alcohols, fatty amides and other fatty moieties, and with propylene oxide and polypropylene oxides.

In an embodiment, the oral composition includes a surfactant system that is sodium lauryl sulfate (SLS).

Optionally, the orally acceptable vehicle comprises sorbitol which is present in an amount of from 10 to 25 wt % based on the weight of the composition, further optionally from 12 to 18 wt % based on the weight of the composition.

According to another aspect of this invention, there is provided a two-phase toothpaste packaged in a package for forming a striped strip when the toothpaste is extruded as a strip from the package. At least one of the two phases of the two-phase toothpaste comprises the toothpaste composition of the invention as described above, which comprises an orally acceptable vehicle, an abrasive comprising calcium carbonate particles and a binder system comprising guar gum and at least one cellulose polymer.

Optionally, the two-phase toothpaste comprises a first white phase of the two-phase toothpaste, the first white phase having the toothpaste composition according to the invention and a second colored phase. The second colored phase may comprise a toothpaste composition according to the invention and a colorant. Alternatively, the second colored phase may comprise an alternative toothpaste composition or a gel.

The use, in a striped toothpaste including a white toothpaste phase comprising calcium carbonate particles as an abrasive and a colored phase, of a binder system in the white toothpaste phase which comprises guar gum and at least one cellulose polymer can minimize mixing of the white toothpaste phase and the colored phase after the striped toothpaste has been extruded as a strip from a package.

The oral care composition may include any other therapeutic, cosmetic, and/or aesthetic materials as may be desired. Examples include desensitizing agents (e.g. a nitrate salt, an arginine ester, a bicarbonate salt, potassium nitrate, an arginine-bicarbonate-phytate complex, potassium citrate, and arginine, among others), a chemical whitening agent (such as a peroxide releasing compound), an opaque whitening agent (such as hydroxyapatite) and an anticalculus agent.

The composition according to the invention may also comprise one or more further agents typically selected from an anti-plaque agent, a whitening agent, desensitizing agent, antimicrobial agent, antibacterial agent, cleaning agent, a flavouring agent, a sweetening agent, adhesion agents, surfactants, foam modulators, abrasives, pH modifying agents, humectants, mouth feel agents, colorants, abrasive, tartar control (anticalculus) agent, fluoride ion source, saliva stimulating agent, nutrient and combinations thereof. The compositions of the invention optionally comprise a fluoride ion source and useful, for example, as an anti-caries agent. Any orally acceptable particulated fluoride ion source can be used, including potassium, sodium and ammonium fluorides and monofluorophosphates, stannous fluoride, indium fluoride, amine fluorides such as olaflur (N'-octadecyltrimethylendiamine-N,N,N'-tris(2-ethanol)-dihydrofluoride), and mixtures thereof. One or more fluoride ion sources are optionally present in an amount providing a clinically efficacious amount of soluble fluoride ion to the oral composition. Optionally, the toothpaste composition further comprises sodium monofluorophosphate in an amount of from 0.75 to 1.5 wt % based on the weight of the composition.

Colorants may be used in a single phase toothpaste or a two-phase toothpaste for forming a striped toothpaste. Such colorants may be selected from pigments, dyes, lakes and agents imparting a particular luster or reflectivity such as pearling agents. In various embodiments, colorants are operable to provide a white or light-colored coating on a dental surface, to act as an indicator of locations on a dental surface that have been effectively contacted by the composition, and/or to modify appearance, in particular color and/or opacity, of the composition to enhance attractiveness to the consumer. Any orally acceptable colorant can be used, including FD&C dyes and pigments, talc, mica, magnesium carbonate, magnesium silicate, silica, titanium dioxide, zinc oxide, red, yellow, brown and black iron oxides, ferric ammonium ferrocyanide, manganese violet, ultramarine, titanated mica, bismuth oxychloride, and mixtures thereof. One or more colorants are optionally present in a total amount of about 0.001% to about 20%, for example about 0.01% to about 10% or about 0.1% to about 5%.

Optionally, the toothpaste composition further comprises titanium dioxide in an amount of from 0.05 to 0.15 wt % based on the weight of the composition. Such titanium dioxide addition has been found to whiten the slightly yellowish appearance of the toothpaste caused by the addition of the guar gum binder.

The toothpaste composition of the invention may be prepared by any means known in the art.

In some embodiments, the manufacturing method comprises a first step wherein guar gum is dispersed into a first aqueous medium which is in a first tank, optionally including a mixer (not shown). The first aqueous medium 4 comprises sorbitol, optionally an aqueous solution of sorbitol. The first aqueous medium is typically at a temperature of from 20 to 40° C.

This dispersion step produces a first gellant dispersion including hydrated guar gum in a sorbitol solution. In the first gellant dispersion, the guar gum is substantially fully hydrated, and substantially fully dissolved in the sorbitol solution to form a first gel phase. Typically, the first gellant dispersion comprises from 0.2 to 4.0 wt % guar gum and from 96.0 to 99.8 wt % sorbitol, each being based on the weight of the first gellant dispersion.

In some embodiments, the manufacturing method comprises a second step, which may be before, after or simultaneous with the first step, wherein at least one cellulose polymer, as described above, is dispersed into a second aqueous medium to produce a second gellant dispersion including hydrated cellulose polymer in an aqueous solution. The second gellant dispersion forms a second gel phase, in which the at least one cellulose polymer is fully hydrated and fully dissolved. The second aqueous medium is typically at a temperature of from 60 to 90° C.

In some embodiments, the second gellant dispersion comprises from 1.4 to 11.0 wt % of the at least one cellulose polymer and from 89.0 to 98.6 wt % water, each being based on the weight of the second gellant dispersion. The second aqueous medium may further comprise at least one toothpaste ingredient selected from a source of fluoride ions, optionally sodium monofluorophosphate, a sweetener, optionally sodium saccharin, and additionally any acid or base required to adjust the pH of the composition, such as a bicarbonate salt, optionally sodium bicarbonate, and a carbonate salt, optionally sodium carbonate.

In some embodiments, the at least one cellulose polymer, such as carboxymethyl cellulose, is provided as a powder and pumped by an eductor into a gel tank. Water, optionally including the at least one toothpaste ingredient dissolved or dispersed therein, is stored in a supply tank and supplied therefrom into the gel tank. The gel tank optionally includes a mixer (not shown). In some embodiments, the second gellant dispersion is formed in the gel tank.

In some embodiments, the first and second gellant dispersions are thereafter combined to form a third gellant dispersion. In some embodiments, the first gellant dispersion is supplied from the first tank into the gel tank which already contains the second gellant dispersion and the first and second gellant dispersions are mixed together to form a homogeneous mixed gel phase.

In some embodiments, the third gellant dispersion is thereafter mixed with a plurality of toothpaste components. The toothpaste components may include an abrasive comprising calcium carbonate particles to form a toothpaste composition. In some embodiments, the third gellant dispersion is supplied from the gel tank into a mixer, and additional component tanks supply additional components such as, respectively, abrasive, flavour and surfactant. Any water insoluble agents, such as triclosan, may be solubilized in the flavor oils to be included in the toothpaste. Additional components such as pigments, such as $TiO_2$, may be added at this stage to mixer. The resultant mixture is agitated until a homogeneous toothpaste composition is formed.

In the mixer, which may be a high speed/vacuum mixer, the mixture is typically mixed at high speed for a period in the range from 5 to 30 minutes, typically under a vacuum of 20 to 50 mm of Hg. The resultant product is a homogeneous, semi-solid, extrudable paste.

The toothpaste composition according to the invention may be administered to or applied to a human or other animal subject. The composition is suitable for administration or application to the oral cavity of a human or animal subject.

The following examples further describe and demonstrate illustrative embodiments within the scope of the present invention. The examples are given solely for illustration and are not to be construed as limitations of this invention as many variations are possible without departing from the spirit and scope thereof. Various modifications of the invention in addition to those shown and described herein should be apparent to those skilled in the art and are intended to fall within the appended claims.

EXAMPLES

Rheology/Tailing

Examples 1 to 3 and Comparative Examples 1 and 3

Toothpaste compositions having the formula indicated in Table 1 was prepared. All amounts are in wt %.

TABLE 1

| Ingredient | Ex. 1 | Ex. 2 | Ex. 3 | Comp. Ex. 1 | Comp. Ex. 2 | Comp. Ex. 3 |
|---|---|---|---|---|---|---|
| Sorbitol (70 wt % aqoeus) solution | 21.0 | 21.0 | 21.0 | 21.0 | 21.0 | 21.0 |
| Guar gum | 0.10 | 0.15 | 0.20 | — | — | — |
| Xanthan gum | — | — | — | — | 0.2 | — |
| MAS | — | — | — | — | — | 1.0 |
| Sodium saccharin | 0.27 | 0.27 | 0.27 | 0.27 | 0.27 | 0.27 |
| Sodium monofluorophosphate | 1.10 | 1.10 | 1.10 | 1.1 | 1.1 | 1.10 |
| CMC | 1.0 | 1.0 | 1.0 | 1.3 | 1.0 | 1.0 |
| Sodium bicarbonate | 0.1 | 0.1 | 0.1 | 0.1 | 0.1 | 0.1 |
| Sodium carbonate | 0.4 | 0.4 | 0.4 | 0.4 | 0.4 | 0.4 |
| Silica | 2.0 | 2.0 | 2.0 | 2.0 | 2.0 | 2.0 |
| Calcium carbonate | 42.0 | 42.0 | 42.0 | 42.0 | 42.0 | 42.0 |
| Titanium dioxide | 0.1 | 0.1 | 0.1 | — | — | — |
| Sodium lauryl sulfate | 2.0 | 2.0 | 2.0 | 2.0 | 2.0 | 2.0 |
| Methyl paraben | 0.1 | 0.1 | 0.1 | 0.1 | 0.1 | 0.1 |
| Propyl paraben | 0.02 | 0.02 | 0.02 | 0.02 | 0.02 | 0.02 |
| Deionized water | 28.81 | 28.76 | 28.71 | 28.71 | 28.81 | 28.01 |
| Flavor | 1.0 | 1.0 | 1.0 | 1.0 | 1.0 | 1.0 |
| Total | 100 | 100 | 100 | 100 | 100 | 100 |

TABLE 1A

| Ingredient | Ex. 1 | Ex. 2 | Ex. 3 |
|---|---|---|---|
| Sorbitol (70 wt % aqoeus solution) | 21.0 | 21.0 | 21.0 |
| Guar gum | 0.10 | 0.15 | 0.20 |
| Xanthan gum | — | — | — |
| MAS | — | — | — |
| Sodium saccharin | 0.27 | 0.27 | 0.27 |
| Sodium monofluorophosphate | 1.10 | 1.10 | 1.10 |
| CMC | 1.0 | 1.0 | 1.0 |
| Sodium bicarbonate | 0.1 | 0.1 | 0.1 |
| Sodium carbonate | 0.4 | 0.4 | 0.4 |
| Silica | 2.0 | 2.0 | 2.0 |
| Calcium carbonate | 42.0 | 42.0 | 42.0 |
| Titanium dioxide | 0.1 | 0.1 | 0.1 |
| Sodium lauryl sulfate | 2.0 | 2.0 | 2.0 |
| Methyl paraben | 0.1 | 0.1 | 0.1 |
| Propyl paraben | 0.02 | 0.02 | 0.02 |
| Deionized water | 28.8033 | 28.7533 | 28.7033 |
| Flavor | 1.0 | 1.0 | 1.0 |
| CI Pigment Green 7 | 0.0067 | 0.0067 | 0.0067 |
| Total | 100 | 100 | 100 |

The compositions of Examples 1 to 3 vary in the amount of guar gum, ranging between 0.1, 0.15 and 0.2 wt %.

The composition of Comparative Example 1 represents a known composition containing carboxymethyl cellulose as a binder, but no guar gum. The composition of Comparative Example 2 represents a composition containing xanthan gum and carboxymethyl cellulose as a binder system, but no guar gum. The composition of Comparative Example 3 represents a known composition containing carboxymethyl cellulose and MAS as a binder system, but no guar gum.

The viscosity of the compositions of Examples 1 to 3 was evaluated over an aging test of a period of 1 week, and compared to the corresponding viscosity of the composition of Comparative Example 3. It was found that the final viscosity, after a period of 1 week, of the composition of Example 3 was rather high as compared to this known comparative compositions and that the initial viscosity of the composition of Example 1 was rather low as compared to this known comparative composition. However, the initial viscosity and final viscosity, after a period of 1 week, of the composition of Example 2 were similar as compared to this known comparative composition. Consequently, although the compositions of Examples 1 and 3 had an acceptable viscosity for use as commercial toothpastes, the rheological properties of composition of Example 2 were further evaluated as compared to the known comparative compositions of Comparative Examples 1 and 3.

During the manufacture, as described above, of the toothpaste compositions of Example 2 and Comparative Examples 1 and 3, the tailing phenomenon was evaluated.

The composition of Example 2 stays on the blade as a common non-flowing mass. In contrast, the composition of Comparative Example 1 flows under gravity to form tails extending downwardly from the blade. Accordingly, it may be seen that the addition of guar gum to the CMC binder composition solves the problem of tailing of the composition. The compositions of the invention, as represented by Example 2, solve the tailing issue in toothpaste compositions including calcium carbonate and CMC.

The composition of Comparative Example 3 stays on the blade as a common non-flowing mass. However, this composition includes MAS which, as discussed above, increases the cost of the composition. Therefore the use of guar gum as a replacement for MAS can provide equivalent rheological properties at lower manufacturing cost.

Other rheological properties of the compositions of Examples 1 to 3 were tested; in particular, the flow property, thixotropy, yield stress and creep recovery, and these results showed that the binder system of CMC and guar gum provided three dimensional structure to the toothpaste compositions of the invention.

In summary therefore, the inventors have found by their experimental investigations and results that that the binder system of CMC and guar gum provided in the calcium carbonate-containing toothpaste compositions of the invention had the desired viscosity and rheology and also solved the problem of stringiness and tailing in known toothpaste formulations.

Stripe Quality

Example 2 and Comparative Examples 2 and 3

The compositions of Example 2 and Comparative Examples 2 and 3 were evaluated to determine the ability of these compositions to provide a high quality stripe when used in a striped toothpaste.

In each case, the respective composition shown in Table 1 was employed to make a striped toothpaste, forming a first white phase. The second colored phase comprised of the composition shown in Table 1A.

The stripe quality was tested by extruding the striped toothpaste and quantitatively evaluating the stripe quality according to a stripe quality index (SQI) numerical scale where 1 represents the worst stripe quality and 5 represents the best stripe quality. Ten data points were employed for the testing of each toothpaste, each data point corresponding to a respective property of a respective extrusion (A=stripe definition, B=stripe consistency of the first short ribbons during extrusion, C=stripe definition, D=stripe consistency of the first long ribbons during extrusion, E=stripe definition, F=stripe consistency of the second short ribbons during extrusion; G=stripe definition, H=stripe consistency of the second long ribbons during extrusion; I=stripe definition, J=stripe consistency of the last short ribbons during extrusion).

The results are shown in Table 2 (below):

TABLE 2

| Stripe Quality Index | Ex. 2 | Comp. Ex. 2 | Comp. Ex. 3 |
|---|---|---|---|
| A | 3.0 | 1.0 | 3.0 |
| B | 2.5 | 1.0 | 3.0 |
| C | 5.0 | 1.5 | 3.75 |
| D | 5.0 | 1.5 | 3.5 |
| E | 5.0 | 1.5 | 4.5 |
| F | 5.0 | 1.5 | 4.5 |
| G | 5.0 | 1.5 | 4.5 |
| H | 5.0 | 2.5 | 4.5 |
| I | 0.4 | 1.5 | 4.5 |
| J | 2.0 | 1.5 | 4.0 |
| Average SQI value | 4.1 | 1.5 | 4.0 |

Replacing 1 wt % MAS by 0.15 wt % guar gum, to form the composition of Example 2, provided good stripe quality, in fact slightly improved stripe quality overall and measurably improved stripe quality over the bulk of the extrusion process, as compared to Comparative Example 3, with a clean separation between the white phase and the colored stripe. This composition according to the invention therefore can produce a high quality striped toothpaste at lower manufacturing complexity and cost than the known MAS-containing compositions.

In contrast, replacing 1 wt % MAS by 0.20 wt % xanthan gum, to form the composition of Comparative Example 2, provided poor stripe quality, with a poor separation between the white phase and the colored stripe.

A comparison between Example 2 and Comparative Example 2 shows surprisingly that guar gum can provide significantly improved strip quality as compared to xanthan gum in a toothpaste composition containing calcium carbonate.

In summary therefore, the inventors have found by their experimental investigations and results that that the binder system of CMC and guar gum provided in the calcium carbonate-containing toothpaste compositions of the invention not only had the desired viscosity and rheology and solved the problem of stringiness and tailing in known toothpaste formulations, but also provided high stripe quality in striped toothpastes.

What is claimed is:

1. A toothpaste composition comprising:
    an orally acceptable vehicle,
    an abrasive comprising calcium carbonate; and
    a binder system comprising guar gum and at least one cellulose polymer;
    wherein the binder system is substantially free of magnesium aluminum silicate, and wherein the guar gum is present in an amount of from 0.13 to 0.17 wt % based on the weight of the composition;
    wherein the guar gum is chemically unmodified guar gum;
    wherein the composition comprises sodium monofluorophosphate in an amount of from 0.75 to 1.5 wt % based on the weight of the composition; and
    wherein the at least one cellulose polymer is present in an amount of from 0.5 to 2.5 wt % based on the weight of the composition.

2. The toothpaste composition according to claim 1 wherein the guar gum is raw guar gum.

3. The toothpaste composition according to claim 1 wherein the calcium carbonate particles are present in an amount of from 20 to 60 wt % based on the weight of the composition.

4. The toothpaste composition according to claim 3 wherein the calcium carbonate is present in an amount of from 35 to 50 wt % based on the weight of the composition.

5. The toothpaste composition according to claim 4 wherein the calcium carbonate is present in an amount of from 40 to 45 wt % based on the weight of the composition.

6. The toothpaste composition according to claim 1 wherein the at least one cellulose polymer is selected from one or more of hydroxypropylmethyl cellulose (HPMC), hydroxyethylpropyl cellulose (HEPC), hydroxybutylmethyl cellulose (HBMC), and carboxymethyl cellulose (CMC).

7. The toothpaste composition according to claim 6 wherein the at least one cellulose polymer comprises carboxymethyl cellulose (CMC).

8. The toothpaste composition according to claim 6 wherein the at least one cellulose polymer is present in an amount of from 0.75 to 1.5 wt % based on the weight of the composition.

9. The toothpaste composition according to claim 8 wherein the guar gum is present in an amount of about 0.15 wt % based on the weight of the composition and carboxymethyl cellulose (CMC) is present in an amount of about 1 wt % based on the weight of the composition.

10. The toothpaste composition according to claim 1 wherein the binder system comprises less than 0.5% of magnesium aluminum silicate.

11. The toothpaste composition according to claim 1 wherein the orally acceptable vehicle comprises sorbitol which is present in an amount of from 10 to 26 wt % based on the weight of the composition.

12. The toothpaste composition according to claim 11 wherein the sorbitol is present in an amount of from 18 to 24 wt % based on the weight of the composition.

13. The toothpaste composition according to claim 1 further comprising a thickener comprising silica particles in an amount of from 1 to 3 wt % based on the weight of the composition.

14. The toothpaste composition according to claim 1 further comprising titanium dioxide in an amount of from 0.05 to 0.15 wt % based on the weight of the composition.

15. A two-phase toothpaste packaged in a package for forming a striped strip when the toothpaste is extruded as a strip from the package, at least one of the two phases of the two-phase toothpaste comprising the toothpaste composition according to claim 1.

16. A two-phase toothpaste packaged in a package for forming a striped strip when the toothpaste is extruded as a strip from the package, which comprises a first white phase of the two-phase toothpaste, the first white phase having the toothpaste composition according to claim 1 and a second colored phase.

17. A two-phase toothpaste packaged in a package for forming a striped strip when the toothpaste is extruded as a strip from the package, which comprises a first white phase of the two-phase toothpaste, wherein the first white phase comprises a toothpaste composition according to claim 1, and the second colored phase comprises a toothpaste composition according to claim 1 and a colorant.

* * * * *